United States Patent [19]
Rydell et al.

[11] Patent Number: 5,514,134
[45] Date of Patent: May 7, 1996

[54] BIPOLAR ELECTROSURGICAL SCISSORS

[75] Inventors: Mark A. Rydell, Golden Valley; Kevin K. Tidemand, Maple Grove, both of Minn.

[73] Assignee: Everest Medical Corporation, Minneapolis, Minn.

[21] Appl. No.: 304,568

[22] Filed: Sep. 12, 1994

Related U.S. Application Data

[63] Continuation-in-part of Ser. No. 13,869, Feb. 5, 1993, abandoned.

[51] Int. Cl.⁶ .................................................. A61B 17/39
[52] U.S. Cl. ........................... 606/50; 606/48; 606/174
[58] Field of Search ................................. 606/48, 50–52, 606/170, 174

[56] References Cited

U.S. PATENT DOCUMENTS

| | | |
|---|---|---|
| 2,691,370 | 10/1954 | Wallace . |
| 3,651,811 | 3/1972 | Hildebrandt et al. . |
| 4,005,714 | 2/1977 | Hiltebrandt . |
| 4,248,231 | 2/1981 | Herczog et al. . |
| 4,862,890 | 9/1989 | Stasz et al. . |
| 5,026,370 | 6/1991 | Lottick . |
| 5,324,289 | 6/1994 | Eggers ................................. 606/48 |
| 5,330,471 | 7/1994 | Eggers ................................. 606/48 |
| 5,391,166 | 2/1995 | Eggers ................................. 606/48 |

FOREIGN PATENT DOCUMENTS

| | | |
|---|---|---|
| 0517244A1 | 12/1992 | European Pat. Off. . |
| 0518230A1 | 12/1992 | European Pat. Off. . |
| WO8500280 | 1/1985 | WIPO . |

OTHER PUBLICATIONS

"Two New Laparoscopic Instruments: Bibolar Sterilizing Forceps and Uterine Manipulator" by Stephen Corson, Medical Instrumentation, vol. 11, No.1.
Cameron–Miller product brochure for Model 80–752.

*Primary Examiner*—Lee S. Cohen
*Attorney, Agent, or Firm*—Haugen and Nikolai

[57] ABSTRACT

A hand operable bipolar scissors instrument comprising two interfacing pivotal blade members which are each an electrode electrically insulated from the other and individually pivotable in relation to each other. Each blade member comprises a substrate base upon which a layer of non-conductive material is secured on the interior surface thereof so that the non-conductive material of each blade member interfaces with that of the other at the meeting surfaces.

4 Claims, 3 Drawing Sheets

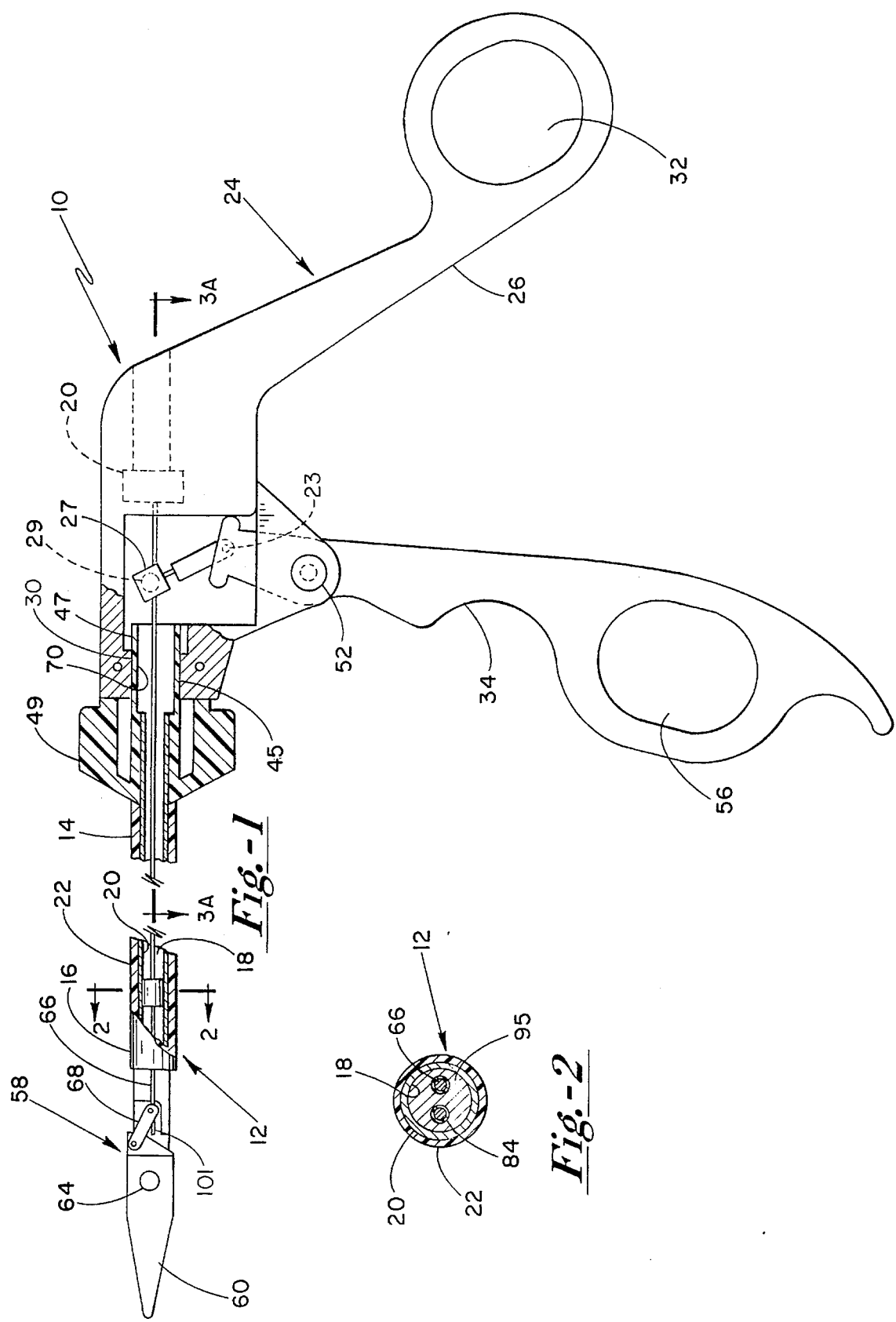

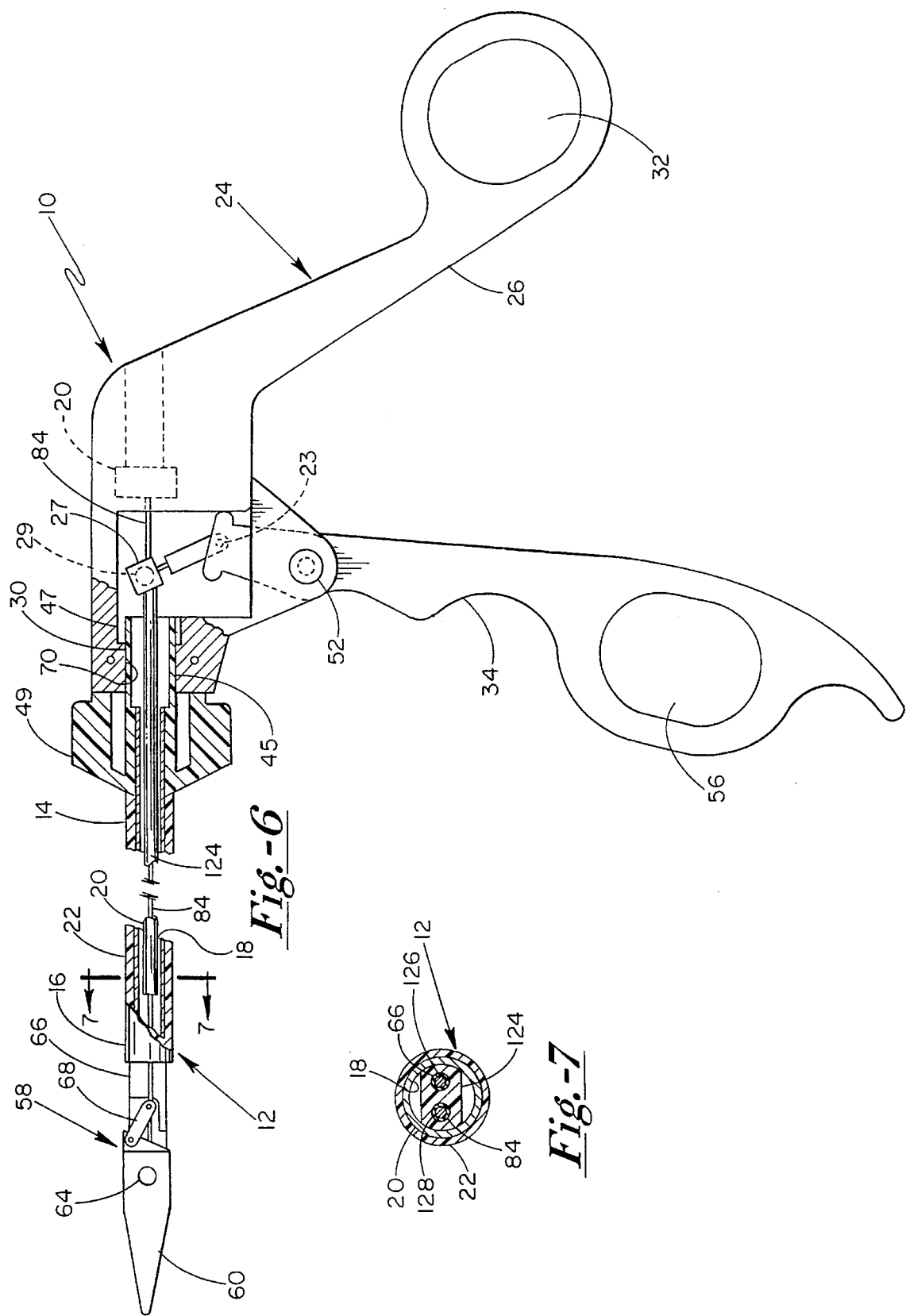

BIPOLAR ELECTROSURGICAL SCISSORS

I. CROSS-REFERENCE TO RELATED APPLICATIONS

This is a continuation-in-part of application Ser. No. 08/013,869, filed Feb. 5, 1993, now abandoned.

BACKGROUND OF THE INVENTION

II. Field of the Invention

This invention relates generally to surgical scissors, and in particular to bipolar scissors wherein both blade members thereof pivot individually and are electrodes to thereby selectively provide direct electrocoagulation of tissue being separated without requiring the introduction of a separate coagulation instrument to the surgical site.

II. Discussion of the Prior Art

Electrocauterization is a process whereby blood vessels (commonly called "bleeders") cut during a surgical procedure are sealed closed by applying electrical energy at the site to, essentially, fuse by heat the vessel opening. In order to provide electrical energy at the site of bleeding, an instrument capable of conducting electricity must be placed at that site. The conductive instrument may be comprised of one electrode (monopolar) which cooperates with a remote conductive body plate electrode, or the instrument may be comprised of two closely spaced electrodes (bipolar). Current passing from one electrode to the other produces the heat sufficient to seal blood vessels or to coagulate blood and other fluids so coagulable. A bipolar instrument is generally preferred by a physician since current travel is over a short distance. A monopolar instrument usually requires electric current to travel a relatively long distance to the body plate electrode, with current directability, and effect being unpredictable and possibly harmful to a patient.

Surgical scissors are known in the art. Those available for use in endoscopically performed surgeries are of a size to fit distally through the endoscope while having operating handles proximally of the endoscope. Generally, the scissors include a proximal scissors-type handle, a central hollow tube through which a linkage from the handle passes, and a distal blade pair to which the linkage connects. Monopolar scissors, wherein both of the scissor blades form one pole and a remote body plate as the second pole, are available. Co-pending and commonly assigned patent application Ser. No. 887,212, filed May 21, 1992, and incorporated herein by reference, teaches a bipolar scissors instrument where each blade thereof is a pole and wherein only one of the scissors' blades pivots in relation to the other blade. A ceramic layer is present on each of the respective inner surfaces of each blade member, and insulation means at strategic sites throughout the instrument maintain bipolar capability for the separate blade members. Double blade movement in bipolar scissors would provide another mechanical attribute which may be beneficial to certain users.

In view of the above discussed prior art, it is a primary object of the present invention to provide bipolar scissors having two blade members wherein each blade member pivots in relation to the other.

It is a further object of the present invention to provide a scissors having dual blade movement and which exhibiting bipolarity for selective application of electrocautery at a surgical site.

These and other objects of the present invention will become apparent in the description of the invention which follows.

SUMMARY OF THE INVENTION

The present invention is a hand operable scissors comprising two interfacing pivotable blade members which are each an electrode electrically insulated from the other and to which current can flow, and further wherein each blade member is individually pivotable in relation to the other blade member. Each blade member comprises a substrate base upon which a layer of nonconductive material is secured on the interior surface thereof so that the nonconductive material of each blade member interfaces with that of the other at the meeting surfaces. The layer of nonconductive material must have adequate structural integrity to function as a shearing force. Preferably, the nonconductive layers are constructed of ceramic. The blade members of the scissors must, of course, meet in a manner to produce a shearing action.

Pivotal movement of the blades is effectuated by two respective rigid rods, each coupled to a respective blade member, extending through a proximally disposed elongated tubular member having disposed at its proximal end a scissors type handle whose hand operation causes the blade members to pivot in relation to each other. Current is delivered to the blades through the rods which are connectable to an RF source and which are electrically insulated throughout the instrument. In this manner, bipolar instruments having cauterization properties as well as tissue separation properties are provided for deployment to the site of a surgical procedure.

BRIEF DESCRIPTION OF THE DRAWINGS

FIG. 1 is a side elevation view of a scissors having two movable blades, the drawing being partially sectioned to illustrate the working elements of the embodiment;

FIG. 2 is a cross-section view along line 2—2 of FIG. 1;

FIG. 6 is a side elevational and partially cross-sectioned view of the bipolar scissors in accordance with an alternative construction; and FIG. 7 a cross-sectional view taken along the line 7-7 in FIG. 6.

DETAILED DESCRIPTION OF A PREFERRED EMBODIMENT

Figure 3A:
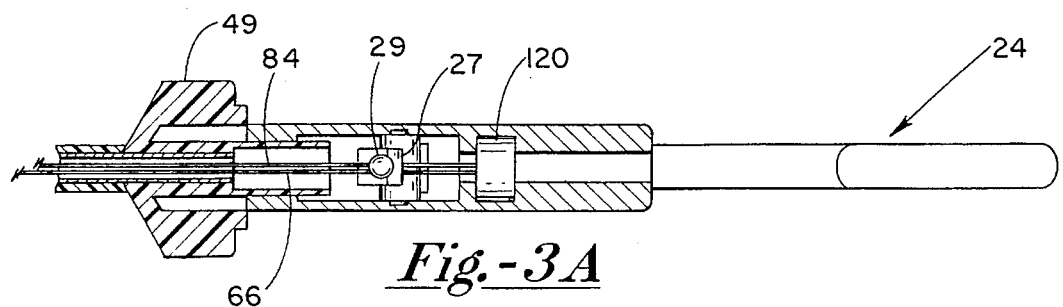
FIG. 3A is a partial top plan view of the proximal portion of FIG. 1.

Referring to FIG. 1, a bipolar electrosurgical scissors 10 is shown for use in endoscopic or other similar scope-type procedures. The scissors 10 has an elongated tubular member 12 of a diameter and length sufficient for use in cooperation with a procedure performed employing scope-type instrumentation. The tubular member 12 has a proximal end 14, a distal end 16 and a lumen 18 which extends for the entire length of the tubular member 12. As shown in the cross-sectional view of FIG. 2, the tubular member 12 comprises a metal tube 20 coated with an electrical insulator 22. The electrical insulator 22 is preferably a polymer such as Teflon®. In addition to being an insulator, such a coating provides a lubricous surface which enhances its slidability through the lumen of an endoscope.

Figure 3B:
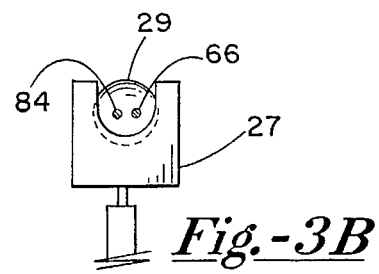
FIG. 3B is a front elevation view of a portion of a coupling for moving the two movable blades.

Disposed at the proximal end 14 of the tubular member 12 is a scissors type handle assembly 24. The handle assembly 24 has a first handle member 26 having first and second ends, with the first end thereof having a bore 30 extending therethrough. The first handle member 26 does not pivot. At its second end the first handle member 26 has a loop 32 intended to receive the thumb of an operator. The handle assembly 24 additionally has a second handle member 34 which is pivotable with respect to the first handle member 26 by being pivotally mounted to the first handle member 26 with a pivot pin 52. The first end of the second handle member 34 has pivotally mounted thereto by pivot pin 23 an open top, U-shaped cradle member 27 shown in detail in FIGS. 3A and 3B in which is cradled a sphere 29 in indirect communication with the distal blade members as described later. Situated at the second end of the handle member 34 is a loop 56 to receive the forefinger of the operator.

Press fit into the distal end 16 of the tubular member 12 is a blade assembly 58. As will be explained more fully later, the blade assembly 58 comprises a first blade member 60 and a second blade member 62 pivotally joined to each other by an insulated rivet or screw 64 which extends through bores formed through the two blade members 60, 62. Both blade members 60, 62 are pivotally movable with respect to each other.

Figure 4:
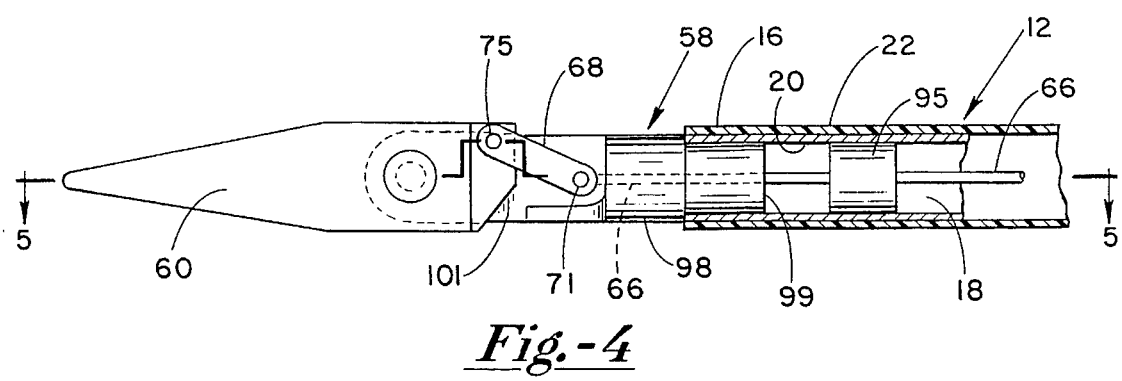
FIG. 4 is an enlarged side elevation view of the distal portion of FIG. 1.
Figure 5:
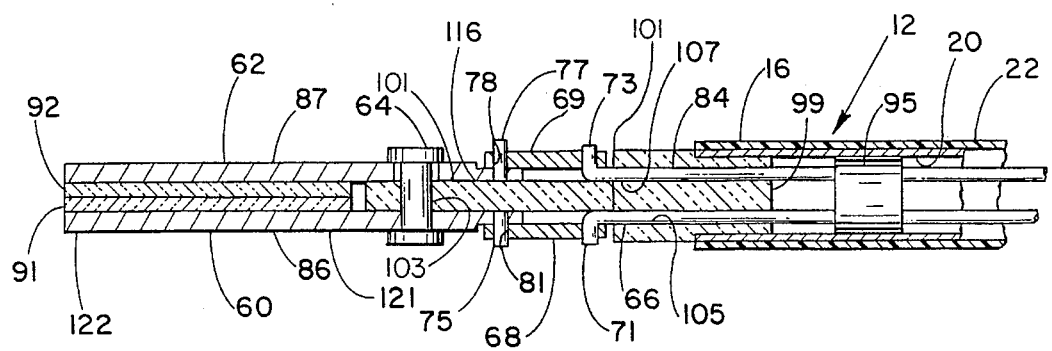
FIG. 5 is a cross-section view along line 5—5 of FIG. 4.

With reference to FIGS. 1 and 2, it is seen that two rigid electrically conductive rods 66, 84, each preferably covered with a layer of electrical insulation, extend through the lumen 18 of the tubular member 12. Referring to FIGS. 1, 4 and 5, which show the distal portion of the scissors 10, the rods 66, 84 are pivotally coupled to the respective blade members 60, 62 by respective rigid links 68, 69. The distal ends of the rods 66, 84 are turned laterally outwardly to fit through respective proximal pivot point openings, 71, 73 of the links 68, 69 and are peened thereafter to form a rivet type connection. Situated at each of the proximal portions of the blade members 60, 62 in step-down sections thereof are laterally projecting posts 75, 77 which pass through distal pivot openings 79, 81 of the links 68, 69 to likewise form rivet type connections. The rigid links 68, 69 thereby can pivot at each of their respective proximal and distal end portions.

As is evident in FIGS. 4 and 5, the blade assembly 58 comprises, in addition to the blade members 60, 62, an insulated hub 98 having a proximal portion 99 and a distal portion 101. The distal portion 101 has a bore 103 therethrough which provides a support to which the blade members 60, 62 are pivotally attached via the pin or screw 64. The proximal portion 99 of the hub 98 is press fit or screwed within the tubular member 12 and has two parallel longitudinal bores 105, 107 through which the rods 66, 84 pass. The hub 98 is preferably formed from ceramic such as zirconia in a molding operation and the opposed flat surfaces of the distal portion 101 are polished to prevent galling of the metal blade surfaces that rub against the flat surfaces during snipping motion of the scissor blades. Longitudinal grooves 102 are formed in the opposed flat surfaces thereof that function to guide the distal end portions of the push rods 66, 84 during actuation of the blades.

Proximal to the hub 98 within the tubular member 12 is disposed an insulator member 95 through which the rod 66, 84 pass. This insulator member 95 functions to electrically isolate the rod 66, 84 from each other while mechanically acting to maintain them together.

The respective proximal ends of the rods 66, 84 extend proximally from the proximal end of the tubular member 12 through the sphere 29 (FIGS. 3A and 3B) and terminate in a free-wheeling electrical connector 120. The free-wheeling connector 120 cannot move translationally in the handle assembly 24, but can freely rotate. External leads originating from an electrosurgical generator (not shown) as known in the art provide current to connector 120 to thereby provide current to the rods 66, 84.

Because the sphere 29 is freely rotatable within the cradle member 27, the tubular member 12, and therefore the blade members 60, 62, can be rotatably moved. A knob 49 is therefore provided near the proximal end of the tubular member 12 to facilitate easy rotation by hand of the blade members 60, 62 when blade member positioning is performed by the operator. As seen in FIG. 1, the rotatable knob 49 is generally cylindrical in shape, having a bore 70 through its center along the central axis. The bore 70 is large enough to accept the tube 20 therein and allow the conductive rods 66, 84 to pass therethrough. The proximal end of the tube 20 is frictionally inserted into the bore 70, to thereby rotate when the knob 49 is rotated. The knob 49 has an integrally formed tubular extension 45 which terminates in an annular flange 47. The handle assembly 24 has complementarily shaped internal contours which accept the extension 45 and the flange 47 to thereby allow rotation thereof within the handle assembly 24. The knob 49 is preferably constructed of nylon so that the extension 45 and annular flange 47 will have lubricous characteristics for smoother rotation inside of the handle assembly 24. Because the rods 66, 84 are mechanically connected by the insulator member 95 which is stationary within the tube 20, rotation of the knob 49 results in rotation of the tube 20 as well as the rods 66, 84 to thereby also rotate the blade members 60, 62. Concurrently, the sphere 29 is rotated because the rods 66, 84 pass therethrough to their termination in the free-wheeling electrical connector 120. As is evident from FIG. 1, operation of the handle assembly 24 by pivotally moving the second handle member 34 moves the cradle member 27 to thereby translationally move the sphere 29 which in turn moves both of the rods 66, 84 to thereby pivotally open and close the blade member 60, 62. In this manner, dual blade movement is accomplished.

Referring to FIGS. 4 and 5, each blade member 60, 62 includes a metal blank 86, 87, preferably stainless steel, to which is bonded on the flat inner surfaces thereof respective electrical insulators such as a ceramic sheet or layer 91, 92 of aluminum oxide or a zirconium ceramic. The layers 91, 92 are each about 0.020 inch, and their working edges are beveled at an angle of about 45 degrees, thereby creating a gap of about 0.040 inch wide between the metal blanks 86, 87 when the blade member 60, 62 are closed. An RF current applied to the blade members 60, 62 can cauterize tissue, vessels and the like which bridge this gap between the metal blanks 86, 87.

To maintain the beveled edges of the ceramic layers 91, 92 in cutting contact, an integrally formed ramp surface 116 is provided to one side of the distal portion 101 of the hub 98 to thereby affect one of the blade members, here shown being blade member 62. The ramp is achieved by appropriately molding or machining the insulated hub 98 so as to leave a rise of approximately 0.005 inch, with the rise being in contact with the proximal portion of the blade 62. When the blade members 60, 62 are affixed to each other, the blade member 62 is bias by the ramp surface 116, thereby forcing the ceramic layers 91, 92 against each other as the blade members 60, 62 are operated. The required shearing action is thereby maintained. Alternatively, shearing action can also be achieved by providing a bend to each blade in a direction toward the other blade, as would be recognized by a skilled artisan.

ALTERNATIVE EMBODIMENT

Referring to FIG. 6, there is shown a slightly modified version of the embodiment of FIG. 1. The ceramic insulator/spacer 95 of FIG. 1 is replaced by an elongated double lumen tube 124 which is preferably formed from nylon or another lubricous polymer and which extends through the lumen 18 of the metal tub 20 substantially the entire length thereof. FIG. 7 shows a cross-sectional view taken through the barrel and the double lumen tube 124. The push rods 66 and 84 extend individually through the separate lumens 126 and 128 and thus remain electrically insulated from one another. In addition to providing this electrical isolation, the double lumen tube 124 also supports the push rods 66 and 84 along substantially their entire length to prevent any bowing thereof when the push rods are in compression upon actuation of the scissors. As such, the scissors blades are made to open and close in a more controlled fashion, improving the "feel" of the device.

It can also be seen in FIG. 7 that the double lumen tube 124 has a somewhat rectangular cross-section that keys into a bore formed in the sphere 29 such that when the knob 49 is rotated, the entire assembly, including the blades, the push rods, the tubular member 12, the push rods 66 and 84 and the double lumen tube 124 rotate as a unit.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

We claim:

1. A hand operable bipolar electrosurgical scissors instrument comprising:
   (a) an elongated tubular member having a proximal end, a distal end, and a lumen extending therebetween;
   (b) two interfacing blade members disposed at the distal end of the tubular member and pivotally joined to one another, said blade members each being an electrode electrically insulated from the other along their respective entire lengths and to which current can flow, and further wherein each blade member is individually pivotable in relation to said elongated tubular member and to the other blade member from an open position to a closed position; and
   (c) a double lumen tube extending along the lumen of the elongated tubular member;
   (d) first and second elongated push rods, each having a proximal end and a distal end, the first and second push rods extending through the lumens of the double lumen tube and individually coupled at their distal ends to the two interfacing blade members; and
   (e) a handle disposed at the proximal end of the tubular member, the handle being coupled to the proximal ends of the first and second push rods and being hand operable to thereby produce pivotable action of the blade members.

2. The instrument as in claim 1 wherein said first and second push rods are electrically conductive and said double lumen tube is electrically nonconductive.

3. The instrument as in claim 2 wherein said lumens of said double lumen tube closely surround the first and second push rods to inhibit their bending when they are subjected to a compressive force.

4. A hand-operable bipolar electrosurgical scissors instrument comprising:
   (a) an elongated tubular member having a proximal end, a distal end, and a lumen extending therebetween;
   (b) an insulating hub member fixedly attached to the distal end of the elongated tubular member and having a pair of parallel, spaced apart, longitudinal bores extending therethrough, the hub member including a distal portion having two opposed generally flat surfaces and a transverse bore extending between the two opposed flat surfaces;
   (c) two interfacing blade members, each pivotally joined to the hub member by a pin extending through said transverse bore and individually abutting said two opposed flat surfaces, said blade members each having an electrode electrically isolated from the other along their respective entire lengths over their full range of movement and to which current can flow;
   (d) first and second electrically conductive push rods supported in parallel, spaced-apart relation along substantially their entire lengths within the lumen of said tubular member and extending from the proximal end of the tubular member and through the longitudinal bores in the hub member and individually pivotally coupled to the two interfacing blade members; and
   (e) a handle disposed at the proximal end of the tubular member, said handle being mechanically coupled to the first and second push rods and being hand operable to thereby produce pivotal action of the blade members.

* * * * *